(12) United States Patent
Berki et al.

(10) Patent No.: US 7,147,639 B2
(45) Date of Patent: *Dec. 12, 2006

(54) DISPOSABLE EXTERNAL FIXATION DEVICE

(75) Inventors: Sandor Berki, Szentes (HU); Antal Insperger, Hodmezovasarhely (HU); Daniele Venturini, Povegliano Veronese (IT)

(73) Assignee: Orthofix S.r.l. (IT)

( * ) Notice: Subject to any disclaimer, the term of this patent is extended or adjusted under 35 U.S.C. 154(b) by 412 days.

This patent is subject to a terminal disclaimer.

(21) Appl. No.: 10/296,793

(22) PCT Filed: Mar. 2, 2001

(86) PCT No.: PCT/EP01/02389

§ 371 (c)(1),
(2), (4) Date: Nov. 26, 2002

(87) PCT Pub. No.: WO01/91655

PCT Pub. Date: Dec. 6, 2001

(65) Prior Publication Data

US 2003/0139744 A1    Jul. 24, 2003

(30) Foreign Application Priority Data

May 26, 2000    (EP)    .................................. 00830380

(51) Int. Cl.
*A61B 17/56*    (2006.01)
*A61F 5/00*    (2006.01)

(52) U.S. Cl. ............................ 606/57; 606/54; 606/86
(58) Field of Classification Search ............ 606/53–59, 606/65, 64, 86
See application file for complete search history.

(56) References Cited

U.S. PATENT DOCUMENTS

| | | | | |
|---|---|---|---|---|
| RE31,809 E | * | 1/1985 | Danieletto et al. | ............ 606/57 |
| 4,621,627 A | * | 11/1986 | DeBastiani et al. | ............ 606/57 |
| 5,087,258 A | * | 2/1992 | Schewior | ............ 606/56 |
| 5,320,622 A | * | 6/1994 | Faccioli et al. | ............ 606/58 |
| 5,951,556 A | * | 9/1999 | Faccioli et al. | ............ 606/65 |
| 6,840,939 B1 | * | 1/2005 | Venturini et al. | ............ 606/54 |

FOREIGN PATENT DOCUMENTS

| | | |
|---|---|---|
| WO | WO-94/02078 A1 | 2/1994 |
| WO | 95/16402 A1 | 6/1995 |
| WO | WO-97/03620 A1 | 2/1997 |

* cited by examiner

*Primary Examiner*—Pedro Philogene
(74) *Attorney, Agent, or Firm*—Akerman Senterfitt

(57) ABSTRACT

A novel disposable axial external fixation device for reducing bone fractures, of the type comprising an extendible rod-like middle body and oppositely located bone screw clamps which are articulated to the respective ends of the rod like middle body by means of ball joints. Advantageously, a ball-and-socket joint is mounted to each clamp within a main body with which a clamping mechanism for clamping bone screws clamping is associated or co-operates. Also provided is an ancillary member adapted for releasable association with one end of each clamp to better adapt each clamp for use in different conditions of installation of the fixation device.

9 Claims, 3 Drawing Sheets

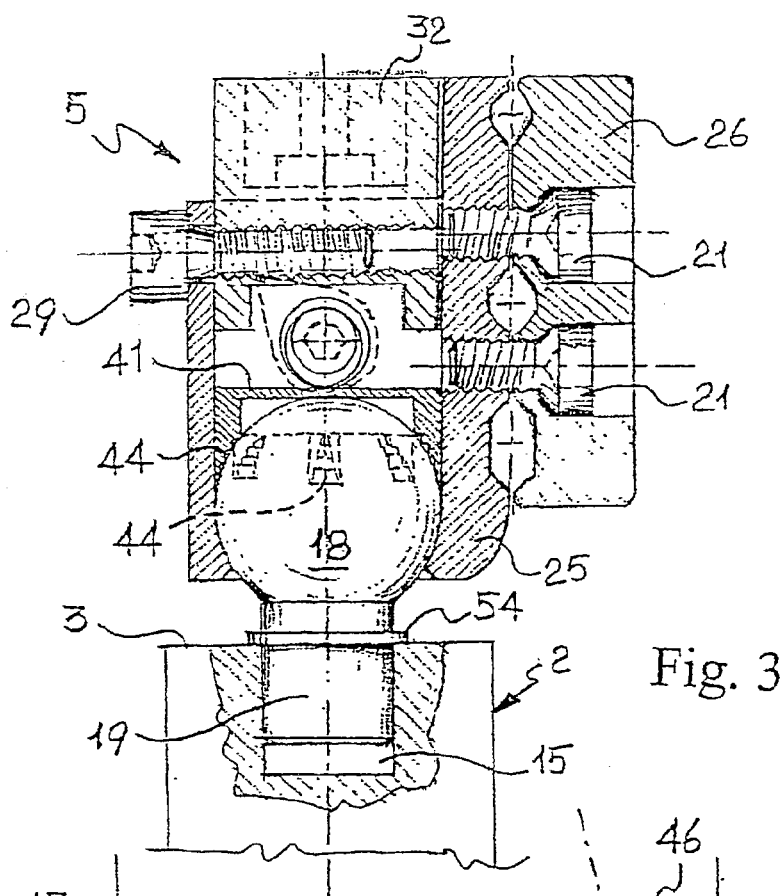
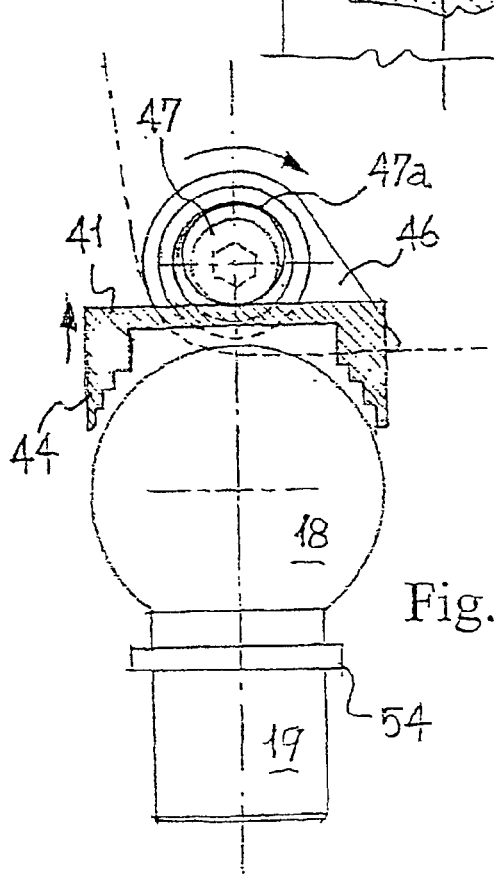
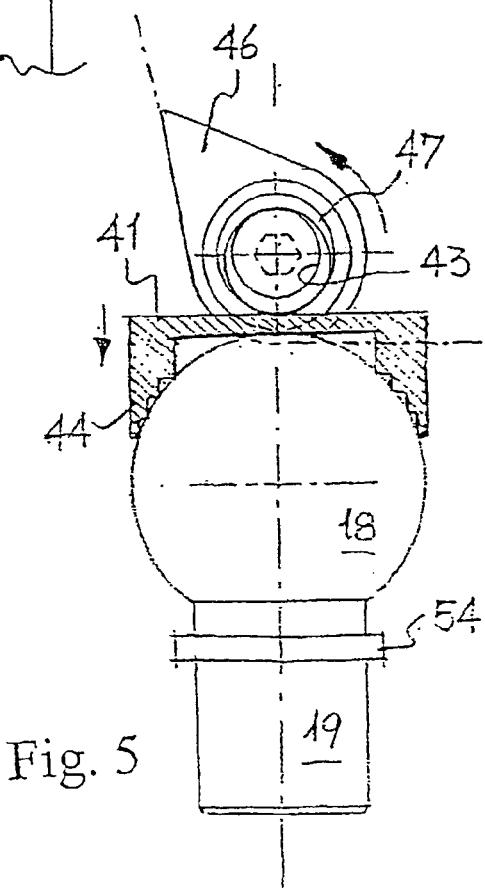
Fig. 3
Fig. 4
Fig. 5

DISPOSABLE EXTERNAL FIXATION DEVICE

FIELD OF THE INVENTION

This invention broadly relates to an improved axial external for stabilizing bone fractures in orthopedic surgery.

More particularly, the invention relates to a disposable axial external fixation device of the type comprising an extendible rod-like middle body and oppositely located bone screw clamps which are articulated to respective ends of the rod-like middle body by means of ball joints.

PRIOR ART

In this specific field, unilateral external fixation devices have been employed to foster recovery of bone fractures, holding the bone fragments firmly in place.

Such external fixation devices usually comprise a middle body of substantially cylindrical shape which is axially extendible and has bone screw clamps articulated to its respective opposite ends by means of ball joints. The clamps are connected to rod-like bone screws which have been implanted into the cortex of a broken bone on opposite sides of the fracture. Usually, two or three screws are adequate to guarantee a hold.

A known external fixation device for stabilizing tibia fractures is disclosed in European patent application No. 0609409 in the name of the same Applicant.

A variety of fixation device to cope with different topologies of fractures and traumatisms are normally available from their suppliers.

Thus, tibia and femur fixators, humerus fixator, joints, such as the ankle and the elbow, fixators and wrist fixators are available.

All these fixation devices are comparable in structure and include similar componentes; however, different types of fractures lead to the necessity of producing a plurality of fixators having different sizes and configurations.

Such a comprehensive stock of different fixators unavoidably reflects in increased manufacturing cost of each typology because of standard mass production methods being impracticable.

Also, the current technological tendency to produce fixators which have portions or parts moulded out of transparent materials to X-radiation makes even less economical the supply of varied and different types of fixators.

The underlying technical problem of this invention is to contrive a unilateral external fixation device, for reducing bone fractures, having structural and functional features which make the device essentially disposable, avoiding a strain of its parts above their support capacity.

SUMMARY OF THE INVENTION

The principle of this invention is that of providing a bone screw clamp with a ball joint mounted to each clamp, and means for locking the ball joint in a prefixed angular position through a permanent set of the ball joint.

Based on this principle, the technical problem is solved according to the invention by fixation device as previously indicated and defined in the characterizing portions of claims 1 and following.

The features and advantages of an external fixation device according to the invention will be apparent from the following description of an embodiment thereof, given by way of the non-limitative example with reference to the accompanying drawings.

BRIEF DESCRIPTION OF THE DRAWINGS

In the drawings:

FIG. 3 shows a further sectional view of a bone screw clamp of the fixation device according to the invention;

FIGS. 4 and 5 show sectional schematic views of a detail of the clamp in FIG. 3 in two different conditions of its operation.

DETAILED DESCRIPTION

Figure 1:
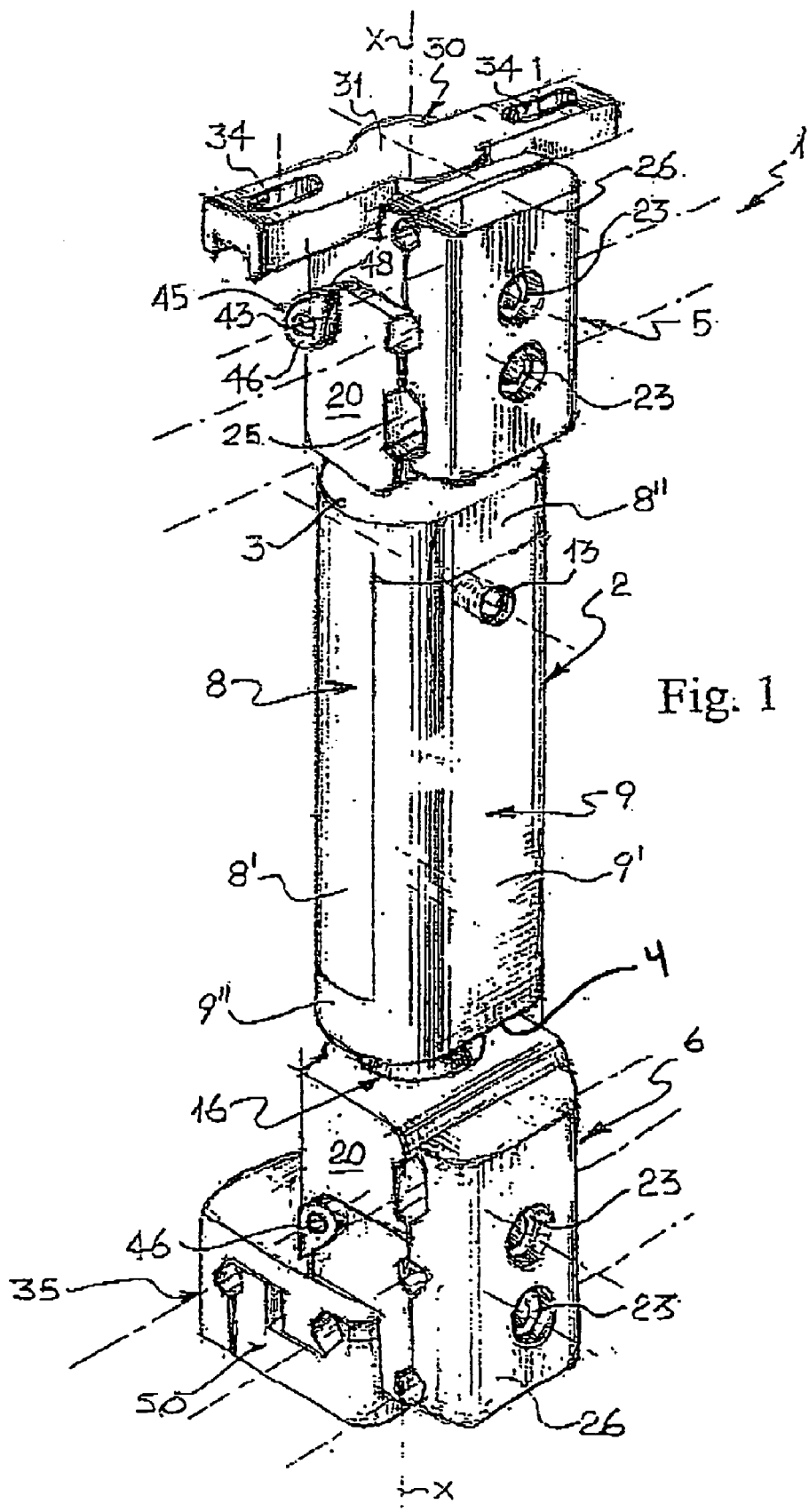
FIG. 1 shows a vertical perspective view of an axial unilateral external fixation device according to this invention.

With reference to the drawing views, an axial unilateral external fixation device for reducing bone fractures in orthopedic surgery, realized according to the present invention, is totally shown at 1.

The fixation device 1 comprises a rod-like middle body 2 having an axis x—x, and having opposite ends 3, 4 which are articulated to the respective bone screw clamps 5, 6.

Advantageously, both the rod-like middle body 2 and the clamps 5, 6 are made out of a transparent material to X-radiation, such as a polyetherketone plastics matrix known as "Peek", which is reinforced with a predetermined amount of carbon fibers in order to obtain a suitable rigidity.

More particularly, the rod-like middle body 2 is axially extendible since it is formed by a first 8 and a second 9 mating parts of prismatic shape. The parts 8 and 9 telescopically slide on each other.

Each of said parts 8, 9 comprises a first portion 8', 9' of elongate semicylindrical shape which is integrally formed with a second cylindrical end portion 8", 9" of short length. Each part, 8 and 9, is therefore L-shaped if seen sideways.

The semicylindrical portions 8', 9' are coupled to each other in a sliding manner by means of a driving groove 7, longitudinally formed in the portion 8', and a corresponding slide 7' longitudinally formed in the other portion 9'. In particular, the portion 8' essentially has a C-shaped section, while the other portion 9' comprises a longitudinal rib having a T-shaped section to define said slide 7'.

Of course, other driving/sliding combinations can be foreseen without coming out of the scope of the invention.

Advantageously, means for stopping said parts 8 and 9 in their sliding movement is provided.

Figure 2:
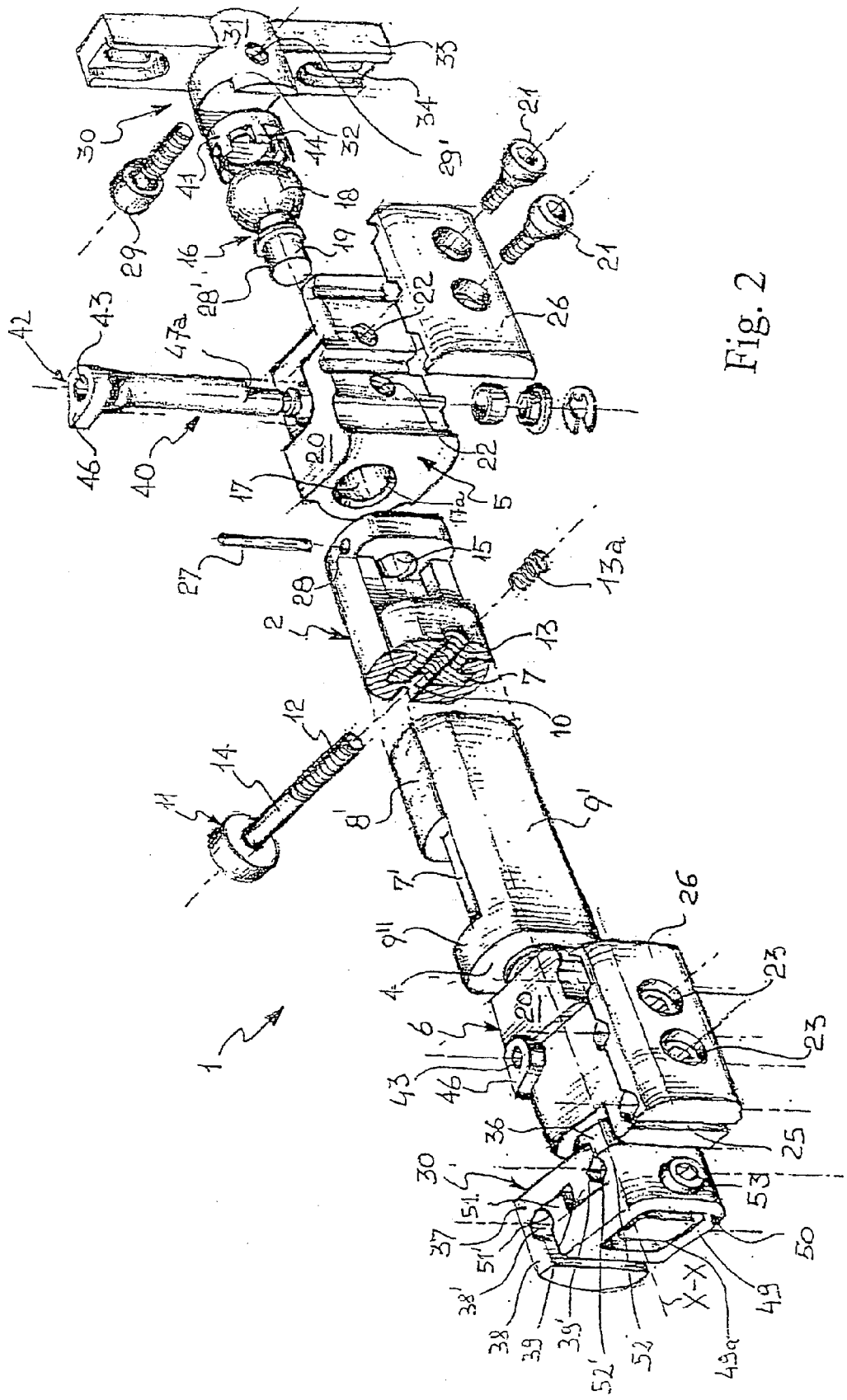
FIG. 2 shows an exploded perspective view of the fixation device shown in FIG. 1.

This stop means comprises a locking screw 11, perpendicularly extended to the axis x—x, which locking screw has a threaded end portion 12 engaged in a threaded hole 13 formed in the slideway 7'. In addition, the portion 8' of the part 8 is formed with a clearance slot 10 which longitudinally spans most of the portion 8, as shown in FIG. 2. The screw 11 goes through the slot 10, preferably with a smooth section of its shank 14, to ease the sliding movement of the portions 8 and 9 on each other.

The screw 11 is a socket head screw (Allen screw) for convenient operation with a wrench.

By loosening and tightening the screw 11, the extension of the rod-like middle body 2 of the fixator 1 can be adjusted as necessary, depending on the different dimensions of the broken bone. On the contrary, no rotations of the parts 8 and 9 about the axis of the rod-like middle body 2 occur, because of the C- and T-shaped sections of the driving groove and of the slide.

In the compact setting of the rod-like middle body 2, the portions 8' and 9' of the parts 8 and 9 are fully superposed, with one abutting the cylindrical end portion 9", 8" of the other.

As mentioned above, the opposite ends 3, 4 of the rod-like middle body 2 are articulated to the respective clamps 5, 6 of the bone screws by means of ball joints.

Each joint comprises a ball-and-socket joint 16 mounted to each clamp 5, 6.

In particular the ball-and-socket joint 16 includes a cylindrical socket 17 which is delimited by a ball-retaining rim 17a and provided in each clamp 5, 6, and a ball head 18 lodged in the socket 17. The ball head 18 has a shank 19 adapted to be received in a corresponding socket 15 on each of the ends 3, 4 of the rod-like middle body 2.

The socket 15 lodging the shank 19 is formed near-centrally in the end portions 8" and 9" of the parts 8 and 9. Briefly, the socket 15 lies along the axis x—x, and the shank 19 is held in the socket 15 by a releasable locking means, such as a lockpin 27 passing through a hole 28 formed transversal to the axis x—x in the portion 8", and a corresponding hole 28' transversal to the shank 19.

Each of the clamps 5 and 6 comprises a main body 20, substantially prismatic in shape, wherein the cylindrical socket 17, which lodges the ball head 18, is formed.

A side flange 26 is removably associated with the main body 20 for constraining the clamp onto bone screws, in the example two screws 21 lying in a plane parallel to the lying plane of the axis x—x, and being placed a predetermined distance away therefrom.

More particularly, the main body 20 has a side wall 25 of shaped contour. The contour of the flange 26 substantially mates with the side wall 25, such that the side wall 25 and the flange 26 will joint join like the jaws of a vise, so locking the bone screws.

Preferably, the removable coupling of the body 20 and the flange 26 occurs by means of the engagement of a pair of screws 21 in corresponding threaded seats 22 provided in the main body 20, through clearance holes 23 in the flange 26. The threaded seats 22 are formed in the side wall 25 of the body 20.

This particular configuration enables the bone screws to be held in the clamp substantially alongside the ball-and-socket joint, thereby achieving a highly compact structure of the overall clamp.

Advantageously, locking means 40 of the ball-and-socket joint 16 in a selected angular position is also provided. This locking means 40 comprises a slider 41 which is guided for movement inside the cylindrical socket 17 of the main body 20 in the direction toward the ball head 18, by the action of a driving means 42.

This driving means 42 comprises a shaft 47 which transversely extends to the socket 17 and is provided with a cam 47a acting on the slider 41. The shaft 47 can be manually rotated with a suitable wrench, and is purposely formed with a recessed hexagon 43 at an accessible end thereof.

Specifically, the slider 41 is formed with a cylindrical rim having a plurality of contrate teeth 44, i.e. all extending towards the same direction parallel to the axis of the rim. These teeth 44 are intended to bite into the surface of the ball head 18, upon actuation of the driving means 42, and form a plurality of impressions of a suitable depth therein, e.g. a few tenths of a millimeter deep. In this way, the ball head 18 becomes set permanently, and the ball-and-socket joint 16 is practically locked in a positive manner.

A stroke limiting means 45 of the slider 41 is provided so that the teeth 44 bite a predetermined depth into the ball head 18. This limiting means 45 comprises a radial nose 46 formed integrally with the shaft 47 and appearing externally of the main body 20, which is arranged to abut against a stop 48 formed on the main body 20, at an appropriate angular setting of the shaft 47 relative to the main body 20.

With the radial nose 46 abutting the stop 48, the plurality of teeth 44 of the slider 41 will have sunk the maximum anticipated depth into the surface of the ball head.

In assembling one of the clamps, 5 or 6, first the ball head 18 of the joint 16 is inserted into the cylindrical socket 17 with the shank 19 abutting out of the main body 20. Then the slider 41 with its teeth 44 facing the ball head 18, and finally the shaft 47 to stop the previous parts from coming off, is assembled. The shaft 47 is positioned such that an end portion of the cylindrical socket 17 is left available for receiving an additional cylindrical member as described herein below.

The cylindrical socket 17 at the free end of the main body 20 is also used for holding an ancillary member 30 which effectively makes the clamp, 5 or 6 more versatile, depending on the different installations of the fixation device.

For example, an ancillary member 30 is illustrated in the drawings by a T-connection member 31, for connecting the clamp 5 to a ring of a ring fixator known in the art as the Ilizarov system.

The connecting member 31 comprises a cylindrical shank 32 pivotally fitted in the same cylindrical socket 17 that accommodates the ball head 18 of the ball-and-socket joint 16.

A locking screw 29 engages in a threaded hole 29', transversely formed at the shank 32 and through a slotted hole provided in the main body 20 close to the end thereof opposite to the ball joint 16. The connecting member 31 further comprises a plate-like portion 33 which is integrally formed with the shank 32 and perpendicularly extends to it. This portion 33 has oppositely located flanges which are penetrated by slotted holes 34 for connection to a ring of an external fixation device of the Ilizarov system.

In this way, a clamp 5 or 6 provided with the connecting member 31 can be fastened to a ring of the Ilizarov system to produce a so-called "hybrid splint", that is an external fixation device comprising an axial fixator and at least one ring, so combining the advantageous features of ring fixation devices and unilateral axial fixation devices.

Another ancillary member 30 is illustrated in the drawings by a metaphysis clamp 35 for clamping to bone screws which lie in a plane substantially perpendicular to the axis x—x and, therefore, transversal to the lying plane containing said bone screws held between the walls 25 and 26 of the clamps 5 or 6.

More particularly, a metaphysis clamp 35 allows to secure the fixation device to bone screws implanted in the proximal or the distal end portions of a tibia, or implanted in the distal end portion of a femur.

The metaphysis clamp 35 is held in one of the clamps 5 or 6, in the same way as the connecting member 31. In fact, the metaphysis clamp 35 would include, as same as the connecting member 31, a cylindrical shank 36 which fits in the cylindrical socket 17, and one end 37 integrally formed with the shank 36 and perpendicularly extended to the latter.

Such a end 37 is configured with a U-shaped portion which is integrally formed with the shank 36, in eccentric position therefrom. Such a U-shaped portion basically comprises a pair of walls 38, 39 extending parallel to and spaced from each other. A semi-cylindrical groove 38', 39' is provided at the bottom of each wall 38, 39 on the same side, which groove defines a semi-socket for accommodating a corresponding metaphysis bone screw, that is a screw implanted in the proximal or the distal end of a tibia, or the distal end of a femur, in a plane substantially perpendicular to the plane of the axis x—x.

Advantageously, the portion 37 includes means for clamping metaphysis bone screws. This clamping means comprises a slider 50 which is mounted on the portion 37 for sliding movement along a direction concurrent to the direction in which the flange 26 is clamped against the wall 25.

Such a slider 50 comprises a rectangular base 49 formed with a window 49a, and has two plate-like lugs 51, 52 which are integrally formed with the base 49 at the short sides thereof.

The plate-like lugs 51, 52 cooperate with the walls 38 and 39 to clamp the metaphysis screws therebetween. More particularly, the slider 50 is sliding mounted on a narrowing end of the wall 39 through the window 49a, such that the lug 51 is faced toward the portion 37 and is movable between the walls 38 and 39, parallel thereto.

At the free ends of the lugs 51 and 52, and on the same side are provided respective semi-cylindrical grooves 51', 52', each defining a semi-socket accommodating a corresponding metaphysis bone screw. With the slider 50 assembled to the portion 37, the grooves 38' and 51' face to each other, and so do the grooves 39' and 52', ready for clamping onto a corresponding metaphysis screw.

A locking screw 53 passes through a hole laterally formed in the slider 50 and engages in a threaded hole formed close to the free end of the wall 39 for locking the slider 50 in place, clamping onto the metaphysis screws.

In this way, i.e. with the screws, including the side ones between the wall 25 and the flange 26, and the metaphysis ones between the slider 50 and the portion 37, all brought to a tightened state by displacements occurring all in the same direction, their mutual positions are retained even when their diameters change, for example, from screws with a diameter of 6 mm to screws with a diameter of 8 mm throughout.

The fixation device of this invention does solve the technical problem and offers a number of advantages, among which the foremost is that the clamps are of universal utility, unlike prior solutions.

In fact, the middle body 2 can have opposite clamps associated with it, which serve different functions but stem all from a common basic structure.

Furthermore, the fixation device made of a transparent material to X-radiation allows the orthopedic surgeon to radiograph the affected region without suffering interference from bulky objects.

Also, it should be noted that the middle body accounts for a major portion of the overall length of the fixation device according to the invention, and allows the fixator length to be adjusted for almost any traumatic situations.

It should be further noted that the multiple impressions produced by the contrate teeth in the surface of the ball head, so that in practice the ball-and-socket joint can be locked in any desired angular position, also forbid re-use of the clamps, which are therefore disposable clamps. This offers an additional advantage from both the sanitary and the safety standpoints.

The invention claimed is:

1. A disposable axial external fixation device for reducing bone fractures comprising:
   an extendible rod-like middle body and oppositely located bone screw clamps which are articulated to respective ends of the rod-like middle body by means of ball joints;
   a ball-and-socket joint mounted to each clamp within a main body; and
   locking means for locking the ball-and-socket joint in a selected angular position is provided through a permanent set of the ball-and-socket joint;
   wherein said ball-and-socket joint comprises a cylindrical socket formed in the main body of the clamp, and a ball head received in the cylindrical socket,
   wherein said locking means comprises a slider which is guided for movement in said socket toward and away from said ball head by the action of driving means, for locking said ball head in a positive manner, the driving means comprising a shaft,
   wherein said slider comprises a plurality of contrate teeth projecting toward a same direction,
   wherein said contrate teeth are adapted to bite into the surface of the ball head and form a plurality of impressions to a suitable depth therein, and
   wherein means for limiting the rotation of the shaft is provided, the means comprising a radial nose integrally formed with the shaft and appearing externally of the main body, the radial nose being adapted to abut against a stop formed on the main body at an appropriate angular setting of the shaft relative to the main body.

2. An external fixation device according to claim 1, wherein the driving means shaft extends transversely to the cylindrical socket and is provided with a cam acting on the slider.

3. An external fixation device according to claim 1, wherein said shaft is manually rotatable with the aid of an appropriate wrench, and is formed with an embedded hexagon at an accessible end.

4. An external fixation device according to claim 1, wherein said clamps are made out of a transparent material to X-radiation.

5. A disposable axial external fixation device for reducing bone fractures comprising:
   an extendible rod-like middle body and oppositely located bone screw clamps which are articulated to respective ends of the rod-like middle body by means of ball joints; and
   an ancillary member releasably associated with a free end of a clamp to enable its connection to another fixation device or to other bone screws;
   wherein a ball-and-socket joint is mounted to each clamp within a main body,
   wherein locking means for locking the ball-and-socket joint in a selected angular position is provided through a permanent set of the ball-and-socket joint,
   wherein said locking means comprises contrate teeth adapted to bite into the surface of the ball head and form a plurality of impressions to a suitable depth therein, and
   wherein said ball-and-socket joint comprises a cylindrical socket formed in the main body of the clamp, and a ball head received in the cylindrical socket; and
   wherein said locking means is guided for movement in said socket toward and away from said ball head.

6. An external fixation device according to claim 5, wherein said ancillary member is rotatably mounted in said cylindrical socket at the free end of said main body.

7. An external fixation device according to claim 6, wherein the ancillary member comprises a cylindrical shank inserted into said cylindrical socket, and a portion transversal to the shank and integrally formed with the latter.

8. An external fixation device according to claim 5, wherein said ancillary member comprises a cylindrical shank inserted into said cylindrical socket, and a metaphysis clamp connected to said shank.

9. An external fixation device according to claim 8, wherein said metaphysis clamp comprises means for clamping metaphysis screws having moving parts which are movable in the same direction as the moving parts of means for clamping bone screws.

* * * * *